(12) United States Patent
Malone

(10) Patent No.: US 9,051,066 B1
(45) Date of Patent: Jun. 9, 2015

(54) SYSTEM AND METHOD FOR FILLING CONTAINERS WITH FLUIDS

(71) Applicant: TINNUS ENTERPRISES, LLC, Plano, TX (US)

(72) Inventor: Joshua Malone, Plano, TX (US)

(73) Assignee: TINNUS ENTERPRISES, LLC, Plano, TX (US)

( * ) Notice: Subject to any disclaimer, the term of this patent is extended or adjusted under 35 U.S.C. 154(b) by 0 days.

(21) Appl. No.: 14/492,487

(22) Filed: Sep. 22, 2014

Related U.S. Application Data

(60) Provisional application No. 61/942,193, filed on Feb. 20, 2014, provisional application No. 61/937,083, filed on Feb. 7, 2014.

(51) Int. Cl.
*B65B 3/04* (2006.01)
*B65B 3/28* (2006.01)
*A63H 27/10* (2006.01)

(52) U.S. Cl.
CPC ... *B65B 3/04* (2013.01); *B65B 3/28* (2013.01); *A63H 2027/1041* (2013.01); *A63H 27/10* (2013.01)

(58) Field of Classification Search
CPC ........... A63H 27/10; A63H 2027/1041; A63H 2027/105; A63H 2027/1033; B65B 3/04; B65B 3/28
USPC .................. 141/234–248, 10, 114; 383/3, 71; 446/220–226
See application file for complete search history.

(56) References Cited

U.S. PATENT DOCUMENTS

| | | | | | |
|---|---|---|---|---|---|
| 262,517 | A | * | 8/1882 | Hendrie | 446/220 |
| 1,098,286 | A | * | 5/1914 | Herbert | 446/222 |
| 1,166,690 | A | * | 1/1916 | Miller | 446/222 |
| 1,350,935 | A | * | 8/1920 | Frank Pastor | 446/222 |
| 1,478,757 | A | * | 12/1923 | O'Connor | 446/222 |
| 1,484,575 | A | * | 2/1924 | Shulin | 239/602 |
| 1,703,463 | A | * | 2/1929 | Weigel | 446/186 |
| 2,027,225 | A | * | 1/1936 | Gill | 446/226 |
| 2,161,274 | A | * | 6/1939 | Behrend | 446/224 |
| 2,553,941 | A | * | 5/1951 | Raab | 446/186 |

(Continued)

FOREIGN PATENT DOCUMENTS

| | | | |
|---|---|---|---|
| FR | 2911512 | * | 7/2008 |
| GB | 294273 | | 7/1928 |

(Continued)

OTHER PUBLICATIONS

Balloon Powered Boat, May 17, 2011, http://alittlelearningfortwo.blogspot.com/.*

(Continued)

*Primary Examiner* — Kevin P Shaver
*Assistant Examiner* — Andrew Stclair

(57) ABSTRACT

An example embodiment of an apparatus includes a housing with an opening at a first end and a plurality of holes at a second end, a plurality of hollow tubes attached to the plurality of holes, a plurality of containers removably attached to the hollow tubes, and a plurality of elastic fasteners, each elastic fastener clamping each container to a corresponding hollow tube, such that when the containers are filled with fluid and detached from the corresponding hollow tubes, each elastic fastener seals each container with the fluid inside.

14 Claims, 6 Drawing Sheets

(56) References Cited

U.S. PATENT DOCUMENTS

| | | | | |
|---|---|---|---|---|
| 2,617,624 | A | 11/1952 | Annis | |
| 2,757,960 | A * | 8/1956 | Hatcher | 239/229 |
| 2,922,252 | A * | 1/1960 | Dam et al. | 446/221 |
| 2,924,041 | A * | 2/1960 | Jackson | 446/224 |
| 3,108,396 | A * | 10/1963 | Isidore | 446/220 |
| 3,118,672 | A * | 1/1964 | Dorn | 473/610 |
| 3,154,050 | A * | 10/1964 | Hanson | 116/210 |
| 3,161,998 | A * | 12/1964 | Lennox | 141/313 |
| 3,301,490 | A * | 1/1967 | Hruby, Jr. | 239/227 |
| 3,368,302 | A * | 2/1968 | Martino | 446/224 |
| 3,580,303 | A * | 5/1971 | Roberge | 141/173 |
| 3,820,200 | A * | 6/1974 | Myers | 24/30.5 S |
| 3,978,555 | A * | 9/1976 | Weisenthal | 24/543 |
| 4,212,460 | A * | 7/1980 | Kraft | 473/577 |
| 4,416,038 | A * | 11/1983 | Morrone, III | 24/487 |
| 4,428,149 | A * | 1/1984 | Brown | 446/222 |
| 4,684,137 | A * | 8/1987 | Armer et al. | 473/609 |
| 4,687,458 | A * | 8/1987 | Handa | 446/222 |
| 4,892,500 | A * | 1/1990 | Lau | 446/221 |
| 4,911,379 | A * | 3/1990 | Kopelman | 244/31 |
| 4,944,709 | A * | 7/1990 | Lovik | 446/221 |
| 5,004,633 | A * | 4/1991 | Lovik | 428/9 |
| 5,029,851 | A * | 7/1991 | Hagen | 273/458 |
| 5,036,985 | A * | 8/1991 | Lovik | 211/13.1 |
| 5,119,281 | A * | 6/1992 | Akman | 362/253 |
| 5,127,867 | A * | 7/1992 | Lau | 446/221 |
| 5,135,222 | A * | 8/1992 | Spector | 473/576 |
| D335,901 | S * | 5/1993 | Gill, III | D21/440 |
| 5,240,450 | A * | 8/1993 | Graham | 446/267 |
| 5,293,707 | A * | 3/1994 | Shaeffer | 40/412 |
| 5,301,392 | A * | 4/1994 | Richman | 24/30.5 R |
| 5,370,161 | A * | 12/1994 | Shafer | 141/114 |
| 5,381,964 | A | 1/1995 | Reyna | |
| 5,439,199 | A | 8/1995 | Briggs et al. | |
| 5,444,962 | A * | 8/1995 | Bonnet | 53/417 |
| 5,496,223 | A * | 3/1996 | Murray | 446/222 |
| 5,509,540 | A * | 4/1996 | Pomerantz | 211/13.1 |
| 5,531,626 | A * | 7/1996 | Deal | 446/473 |
| 5,538,456 | A * | 7/1996 | Liu et al. | 446/473 |
| 5,588,896 | A * | 12/1996 | Goodman | 446/187 |
| 5,628,091 | A * | 5/1997 | Mueller | 24/3.2 |
| 5,639,526 | A * | 6/1997 | Kotsiopoulos et al. | 473/577 |
| 5,732,530 | A * | 3/1998 | Pfaff | 53/403 |
| 5,755,419 | A * | 5/1998 | Gearhart et al. | 248/346.01 |
| 5,826,803 | A * | 10/1998 | Cooper | 239/556 |
| 5,944,576 | A * | 8/1999 | Nelson et al. | 446/220 |
| 5,964,636 | A * | 10/1999 | Carrera | 446/224 |
| 5,975,983 | A * | 11/1999 | Panec | 446/475 |
| 6,007,403 | A * | 12/1999 | Urspringer et al. | 446/222 |
| 6,047,866 | A * | 4/2000 | Brown | 222/608 |
| 6,106,135 | A * | 8/2000 | Zingale et al. | 362/186 |
| 6,149,488 | A * | 11/2000 | Stark | 446/220 |
| 6,158,619 | A * | 12/2000 | D'Andrade et al. | 222/79 |
| 6,176,758 | B1 * | 1/2001 | Wu | 446/224 |
| 6,386,938 | B1 * | 5/2002 | Novak et al. | 446/186 |
| 6,478,057 | B1 * | 11/2002 | Bearss et al. | 141/313 |
| 6,478,651 | B1 * | 11/2002 | Weir | 446/220 |
| 6,527,615 | B1 * | 3/2003 | Boehler | 446/220 |
| 6,558,223 | B1 * | 5/2003 | Matthews | 446/153 |
| 6,598,807 | B1 * | 7/2003 | Anzalone | 239/302 |
| 6,716,083 | B1 * | 4/2004 | Castro | 446/220 |
| 6,793,094 | B2 * | 9/2004 | Turnbough | 220/603 |
| 7,444,938 | B2 * | 11/2008 | Tippmann | 102/498 |
| 7,762,214 | B2 * | 7/2010 | Ritchey | 119/707 |
| 8,037,906 | B1 * | 10/2011 | Grillo | 141/10 |
| 8,141,326 | B2 * | 3/2012 | Wang | 53/284.7 |
| 8,251,111 | B2 * | 8/2012 | Nelson et al. | 141/361 |
| 8,733,675 | B2 * | 5/2014 | Leber | 239/589 |
| 8,789,565 | B1 * | 7/2014 | Wicken | 141/237 |
| 2001/0003505 | A1 * | 6/2001 | Bertrand | 362/101 |
| 2004/0127311 | A1 * | 7/2004 | Brock | 473/577 |
| 2004/0174718 | A1 * | 9/2004 | Ohlund | 362/565 |
| 2005/0004430 | A1 * | 1/2005 | Lee et al. | 600/116 |
| 2005/0138862 | A1 * | 6/2005 | O'Connor | 47/41.12 |
| 2005/0176339 | A1 * | 8/2005 | Cuisinier | 446/220 |
| 2006/0291217 | A1 * | 12/2006 | Vanderschuit | 362/363 |
| 2007/0167107 | A1 * | 7/2007 | Petell et al. | 446/220 |
| 2008/0121309 | A1 * | 5/2008 | Boise et al. | 141/313 |
| 2008/0166943 | A1 * | 7/2008 | Hou | 446/86 |
| 2010/0326212 | A1 * | 12/2010 | Furey et al. | 73/863.31 |
| 2011/0151744 | A1 * | 6/2011 | Archer et al. | 446/222 |
| 2011/0253256 | A1 * | 10/2011 | Finley | 141/98 |
| 2013/0118640 | A1 * | 5/2013 | Saggio | 141/313 |
| 2014/0030452 | A1 * | 1/2014 | Warner et al. | 428/34.1 |
| 2014/0076454 | A1 * | 3/2014 | Kjar | 141/1 |
| 2014/0212074 | A1 * | 7/2014 | Durst | 383/44 |
| 2014/0316207 | A1 * | 10/2014 | Hain | 600/194 |
| 2015/0020480 | A1 * | 1/2015 | Harris et al. | 53/416 |
| 2015/0056887 | A1 | 2/2015 | Harter et al. | |

FOREIGN PATENT DOCUMENTS

| | | | |
|---|---|---|---|
| GB | 1277377 | * | 6/1972 |
| WO | WO2015/027187 | | 2/2015 |

OTHER PUBLICATIONS www.conwinonline.com/shop/air-force4/, accessed Mar. 19, 2015, published Jun. 11, 2013.* https://www.youtube.com/watch?v=-HIZjZII2O8o, accessed Apr. 7, 2015, allegedly published May 12, 2014.

https://www.youtube.com/watch?v=wCajj0KPV7c, accessed Apr. 7, 2015, allegedly published Aug. 19, 2014.

* cited by examiner

US 9,051,066 B1

SYSTEM AND METHOD FOR FILLING CONTAINERS WITH FLUIDS

CROSS-REFERENCE TO RELATED APPLICATIONS

This application claims the benefit of priority under 35 U.S.C. §119(e) to U.S. Provisional Application Ser. No. 61/937,083 entitled "SYSTEM AND METHOD FOR FILLING INFLATABLE CONTAINERS WITH LIQUID" filed Feb. 7, 2014 and to U.S. Provisional Application Ser. No. 61/942,193 entitled "SYSTEM AND METHOD FOR FILLING INFLATABLE CONTAINERS WITH FLUIDS" filed Feb. 20, 2014, which are hereby incorporated by reference in their entireties.

TECHNICAL FIELD

The present disclosure relates generally to fluid inflatable systems and more particularly, to a system and method for filling containers with fluids.

BACKGROUND

Inflatable containers such as balloons can be filled with a variety of fluids, such as air, helium, water, medicines, etc. In some cases, a lot of inflatable containers may need to be filled with fluids. For example, balloons used as props in conventions, large parties, etc. may number in the hundreds and may require substantial human effort to fill them all in a timely manner. In another example, water balloons used as kids' toys may need to be filled in large numbers to aid in various games. Various methods may be employed to fill such inflatable containers. For example, an individual may blow up and tie each balloon by hand or use a tank of compressed air or helium to inflate the balloon, which then has to be tied. In another example, an individual may fill water balloons with water by hand one at a time, and then tie the balloons, which can all be quite time-consuming. Moreover, the inflatable containers may be damaged or filled to different volumes.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Overview

Figure 1:
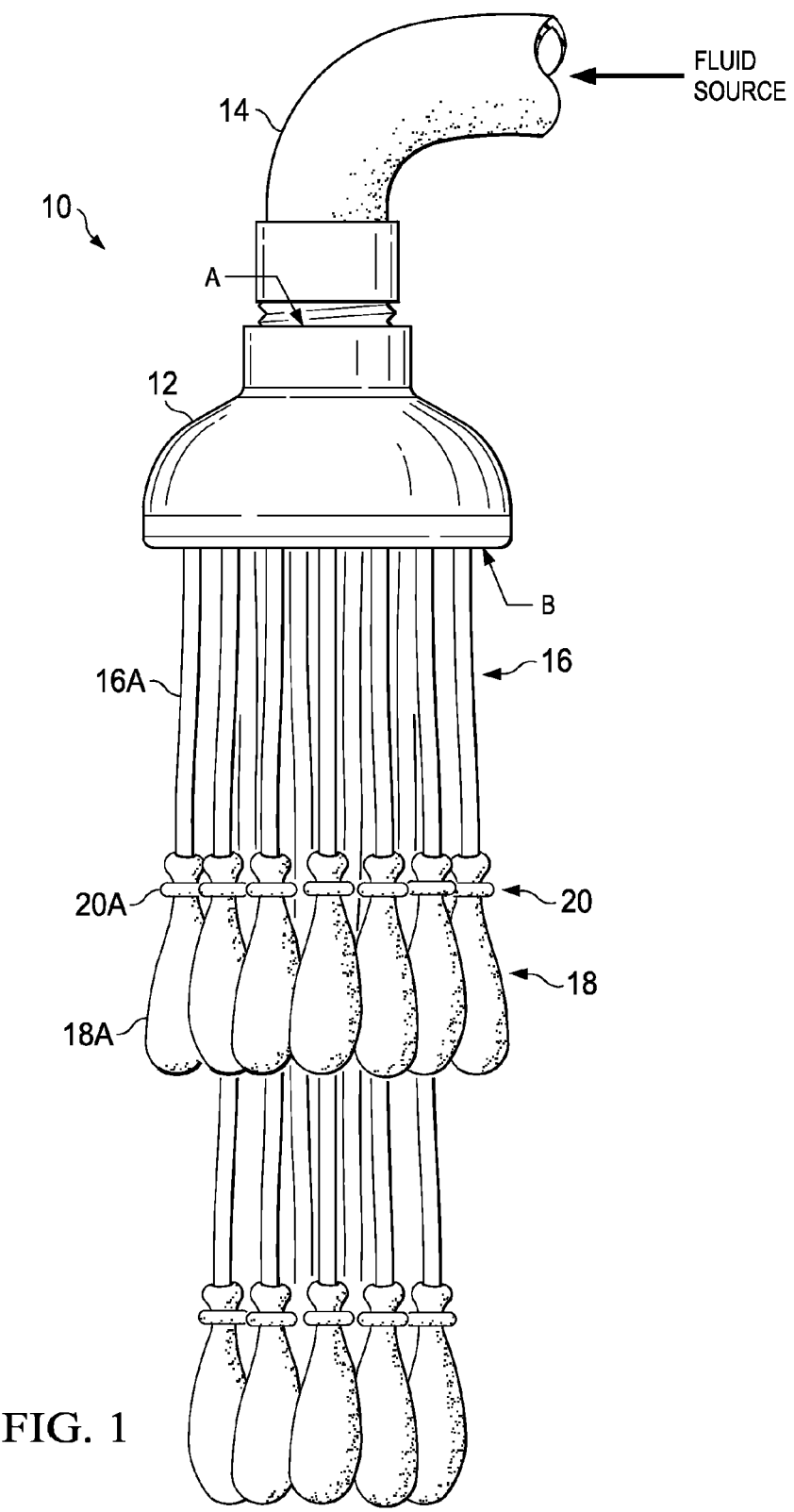
FIG. 1 is a simplified perspective view illustrating an example configuration of an embodiment of a system for filling containers with fluids.

An example embodiment of an apparatus includes a housing (e.g., casing, covering, etc. with a cavity inside) with an opening at a first end and a plurality of holes at a second end, a plurality of hollow tubes attached to the plurality of holes, a plurality of containers (e.g., receptacles, vessels, ampules, test-tubes, balloons, etc.) removably attached to the hollow tubes, and a plurality of elastic fasteners, each elastic fastener clamping each container to a corresponding hollow tube, such that when the containers are filled with fluid and detached from the corresponding hollow tubes, each elastic fastener seals each container with the fluid inside.

Example EMBODIMENTS

It is to be understood that the following disclosure describes several example embodiments for implementing different features, structures, or functions of the system. Example embodiments of components, arrangements, and configurations are described herein to simplify the present disclosure. However, these example embodiments are provided merely as examples and are not intended to limit the scope of the invention.

The present disclosure may repeat reference numerals and/or letters in the various exemplary embodiments and across the Figures provided herein. This repetitions is for the purpose of simplicity and clarity and does not in itself indicate a relationship between the various exemplary embodiments and/or configurations discussed in the various Figures.

FIG. 1 is a simplified diagram illustrating an example embodiment of a system 10 for filling containers with fluids. System 10 includes a housing 12 removably attached to a hose 14 (e.g., tube, pipe, etc.) on a first end A and to a plurality of hollow tubes 16 on a second end B. As used herein, the term "housing" encompasses a hollow space enclosed by a rigid or semi-rigid casing (e.g., covering, skin, sleeve, sheath, etc.). In some embodiments, end A may include a threaded opening configured to mate with corresponding threads on hose 14. In some embodiments, end A may be smaller in circumference or area than end B. Hose 14 may be connected to a fluid source, such as a water tank, gas tank, water supply line, etc. on end A. End B may include a plurality of holes (e.g., configured in an array), configured to fit tubes 16. In some embodiments, tubes 16 may be permanently attached (e.g., welded, brazed, stuck with adhesives, press-fitted, etc.) to housing 12. In other embodiments, tubes 16 may be removably attached (e.g., with threads, pressure, etc.) to housing 12.

A plurality of containers 18 may be clamped (e.g., attached, fastened, held, clinched, secured, etc.) to plurality of tubes 16 using elastic valves 20. As used herein, the term "container" refers to an object that can hold something, such as fluids. The term "valve" refers to an object that regulates, directs, or controls the flow of fluids, by opening, closing, or partially obstructing passageways of fluid flow. In an example embodiment, elastic valves 20 comprise elastic fasteners, such as O-rings. In another example embodiments, elastic valves 20 comprise corrugations, smocking, elastic fibers, etc. fabricated into the necks of containers 18 such that force is required to pull open the necks of containers 18, and removal of the force causes the necks to constrict and close. In yet another example embodiment, elastic valves comprise internal or external plugs affixed to the necks of containers 18, through which tubes 16 may be pushed through to clamp containers 18 thereto.

Note that each of containers 18 have an opening to facilitate clamping to tubes 16 and a cavity for containing fluid. For example, one end of an example tube 16A may be fitted through a hole in end B of housing 12, and the other end of tube 16A may be inserted into an example container 18A. An example elastic valve 20A (e.g., O-ring, comprising a mechanical gasket typically in a toroid shape; elastic ring, such as a rubber-band) of sufficient size to expand and clamp around tube 16A may be dispose around (e.g., placed over) a neck (e.g., portion just below opening) of container 18A, clamping and sealing container 18A to tube 16A. Thus, elastic valve 20A may be in an open configuration when container 18A is attached to tube 16A; in elastic valve 20A's open configuration, the neck of container 18A is open, allowing container 18A to fill with fluid. After container 18A is filled with fluid, it may be removed from tube 16A, whereupon elastic valve 20A closes, thereby closing the neck of container 18A and sealing the fluid inside.

In one example embodiment, containers 18 may comprise inflatable balloons that may be filled with fluids such as water, air or helium. In another example embodiment, containers 18 may comprise flexible (e.g., stretchy, springy, etc.) elastic containers that may be filled with gaseous or liquid medications. As used herein, the term "elastic" is meant to refer to a property of a material that allows the material to resume its normal shape spontaneously after contraction, dilation, or distortion. In an example, an elastic material may be stretched to 200% of its original length, and the material may return to its original length when the stretching force is removed.

In yet another example embodiment, containers 18 may comprise flexible containers that may be filled with body fluids (e.g., urine, blood) for example, to collect multiple samples simultaneously for testing. Virtually any type and kind of fluid may be used within the broad scope of the embodiments. Note that in some embodiments, containers 18 need not be inflatable or flexible in their entireties. For example, a bottom portion of containers 18 may be inelastic (e.g., glass, plastic, metal, etc., of fixed shape and size), and a top portion may be flexible enough to be inserted around tubes 16 and clamped thereon.

When the fluid source is turned on, fluid may flow through housing 12, tubes 16 and fill containers 18. In some embodiments, when housing 12 is connected to a stream of liquid, containers 18 may be filled with the liquid. In some embodiments, the fluid may be supplied at high pressure. Virtually any mechanism that facilitates fluid flow through tubes 16 at sufficient pressure to fill containers 18 may be used within the broad scope of the embodiments. After containers 18 have reached a desired size or volume, they may be detached from tubes 16. In one example embodiment, filled containers 18 may be detached by pulling them away from tubes 16.

In another example embodiment, the connecting force holding filled containers 18 to tubes 16 may be overcome by an upward acceleration on tubes 16, for example, when they are shaken. Thus, filled containers 18 may be detached by shaking housing 12 (or tubes 16) sufficiently vigorously to cause containers 18 to fall off from tubes 16. In some embodiments, the connecting force holding filled container to its corresponding tube is not less than the weight of the filled container; in a specific embodiment, the connecting force holding each container to its corresponding tube is exactly equal to the weight of the filled container. The connecting force may be provided by a combination of constricting forces and friction forces from elastic valves 20.

In yet other embodiments, containers 18 may fall off under gravity; for example, when filled containers 18 reach a threshold weight, they slip off tubes 16 due to gravity. The threshold weight may be based upon the tightness of elastic valves 20, friction between tubes 16 and containers 18, and force from the weight of containers 18 (among other parameters). In various embodiments, containers 14 may slide off tubes 16 and elastic valves 20 may constrict the necks of containers 18, sealing them. In some embodiments, containers 18 may be marked with volumetric measurements, and fluid flow may be turned off when the fluid has filled containers 18 to a desired volume.

In some embodiments, hollow tubes 16 may be made of a rigid material (e.g., steel, glass); in other embodiments, tubes 16 may be made of a flexible material (e.g., thin plastic). In some embodiments, tubes 16 may be thick, short and rigid; in other embodiments, tubes 16 may be slender, long and flexible. Thus, hollow tubes 16 may be flexible, semi-rigid, or rigid, based on its material of construction, design, or a combination thereof. Note that tubes 16 may be of different lengths, for example, to prevent crowding and to accommodate a larger number of containers 18 than would be possible if tubes 16 were of the same length. Thus, at least some of hollow tubes 16 may be of different lengths than the others.

Also, tubes 16 may be flexible to enable containers 18 to expand. Thus, as containers 18 fill with fluid and expand, they may push against each other, flexing tubes 16. The outermost tubes 16 may be flexed more than the innermost tubes 16 (outer and inner being in reference to a center-point of housing 12, with the inner tubes 16 being closer to the center-point, and the outer tubes 16 being farther from the center-point).

Figure 2:
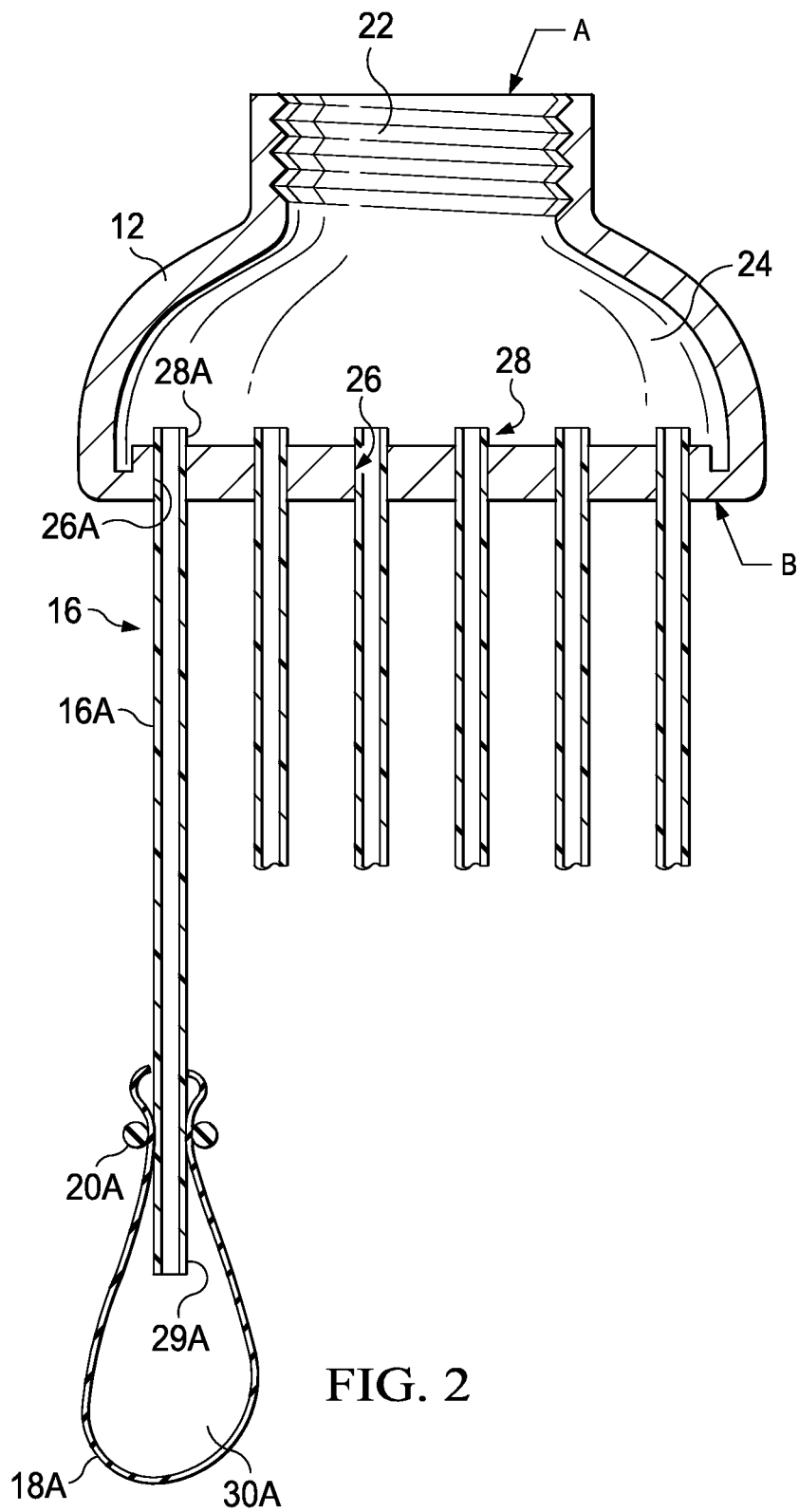
FIG. 2 is a simplified diagram illustrating a cross-sectional view of example details of an embodiment of the system.

Turning to FIG. 2, FIG. 2 is a simplified cross-sectional view of a portion of an embodiment of system 10. Housing 12 comprises a threaded opening 22 at end A, an internal cavity 24, and an array of holes 26 at end B. Internal cavity 24 facilitates distributing the fluid entering at threaded opening 22 to array of holes 26 at end B. In some embodiments, threaded opening 22 may be configured for attaching to a fluid supply hose 14 (e.g., garden hose, plastic tube, etc.). In other embodiments, threaded opening 22 may be attached to corresponding threads in a valve. Array of holes 26 may be configured for connecting first ends 28 of tubes 16 by any suitable means. In some embodiments, first ends 28 of tubes 16 may be connected to corresponding holes 26 by compressing or gluing. In some embodiments, a number of holes 26 in housing 12 and a number of tubes 16 can correspond to a number of containers 18 that are desired to be filled and sealed substantially simultaneously.

To clarify further, only one example tube 16A is shown in the figure. A first end 28A of tube 16A is fitted through a corresponding hole 26A in housing 12. A second end 29A of tube 16A is inserted into container 18A. Elastic valve 20A may be placed around the neck of container 18A clamping the neck to tube 16A. An internal volume 30A of container 18A may be filled with fluid appropriately.

To fill and seal containers 18, housing 12 may be attached to a fluid supply tube (e.g., garden hose) and the fluid supply may be turned on. The fluid enters housing 12, is distributed to holes 26, travels down tubes 16, and fills containers 18. Containers 18 may be filled and may expand substantially simultaneously. When containers 18 have reached a desired size and/or they are filled with the desired volume of fluid, they may be removed from tubes 16. They can be removed by falling off, by shaking them off, by pulling them off by hand, etc. As each container 18A is removed from corresponding tube 16A, respective elastic valve 20A may constrict and close the neck of container 18A, sealing it with the fluid inside.

Figure 3:
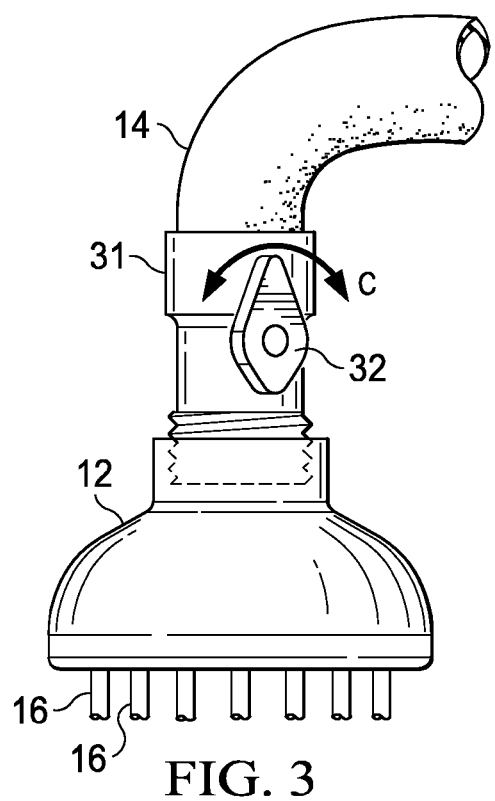
FIG. 3 is a simplified diagram illustrating other example details of an embodiment of the system.

Turning to FIG. 3, FIG. 3 is a simplified diagram illustrating example details of a valve 31 that may be attached between hose 14 and housing 12 according to an embodiment of system 10. One end of valve 31 may be attached to hose 14 and the other end may be attached to threaded opening 22 of housing 12 (e.g., using threads). A lever 32 may be turned from one side (of valve 31) to another (e.g., as indicated by arrow C) to turn on and turn off fluid flow to housing 12. For example, to turn on the fluid flow, lever 32 may be turned to a first position; lever 32 may be turned to a second position (e.g., different from the first position) to turn off fluid flow.

Figure 4:
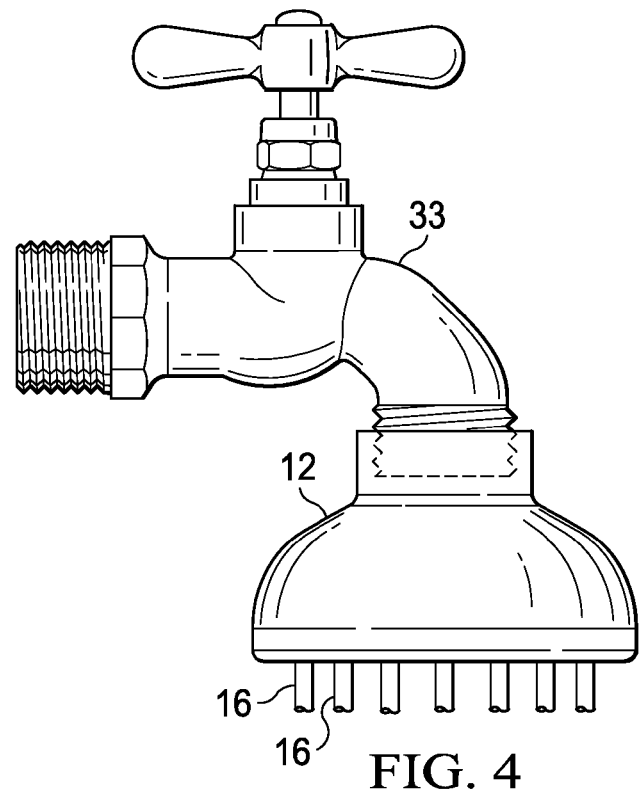
FIG. 4 is a simplified diagram illustrating yet other example details of an embodiment of the system.

Turning to FIG. 4, FIG. 4 is a simplified diagram illustrating example details of an embodiment of system 10. Housing 12 may be attached to a spigot 33 (e.g., nozzle, faucet, outlet, etc.) that connects to the fluid source. Spigot 33 may be turned on or turned off to start or stop fluid flow to housing 12.

Figure 5:
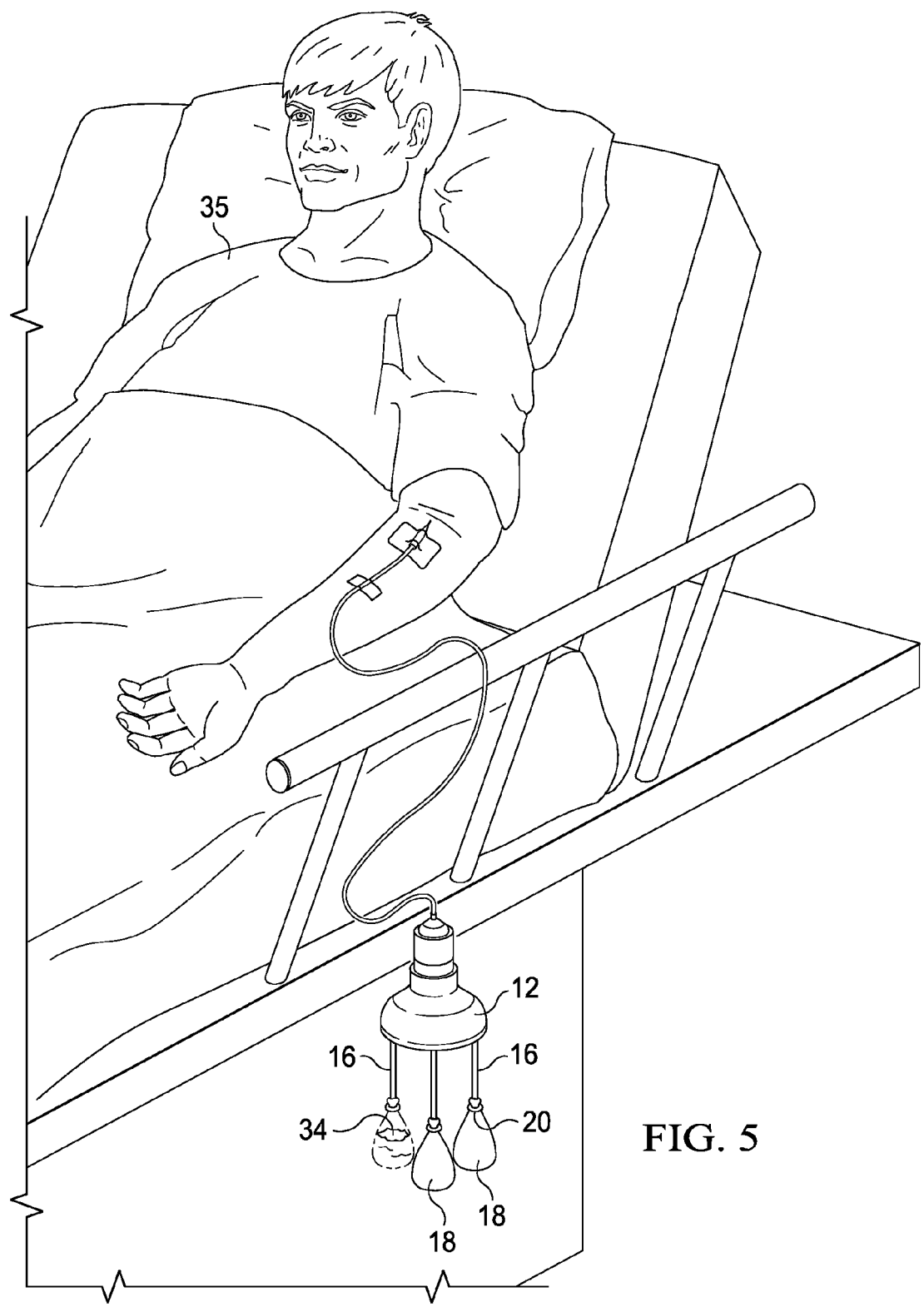
FIG. 5 is a simplified diagram illustrating yet other example details of an embodiment of the system.

Turning to FIG. 5, FIG. 5 is a simplified diagram illustrating example details of an application of an embodiment of system 10. Embodiments of system 10 may be used in a variety of applications, such as for collecting numerous blood samples substantially simultaneously. Blood 34 may be drawn from a human (or animal) and blood 34 may collect substantially simultaneously in plurality of containers 18. The substantial simultaneous collection of blood in such manner can ease patient pain, speed up sampling time, and enable taking multiple samples substantially simultaneously without cross-contamination from one container to another or messy transfers between containers.

Figure 6:
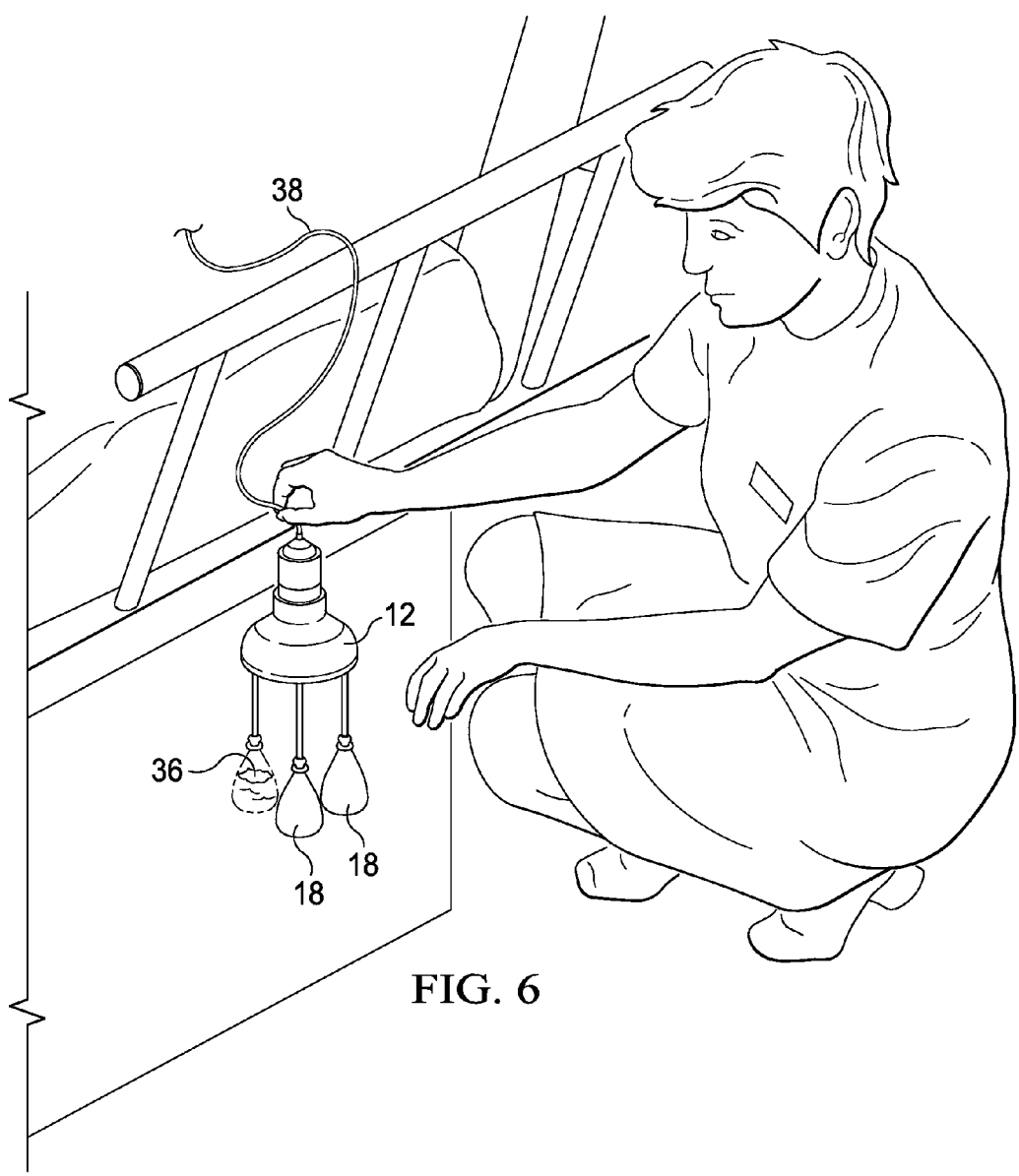
FIG. 6 is a simplified diagram illustrating yet other example details of an embodiment of the system.

Turning to FIG. 6, FIG. 6 is a simplified diagram illustrating example details of an application of an embodiment of system 10. Embodiments of system 10 may be used in a variety of applications, such as for collecting numerous urine samples substantially simultaneously. Urine 36 may be drawn from a human (or animal) through a suitable catheter 38, and may collect substantially simultaneously in plurality of containers 18.

Figure 7:
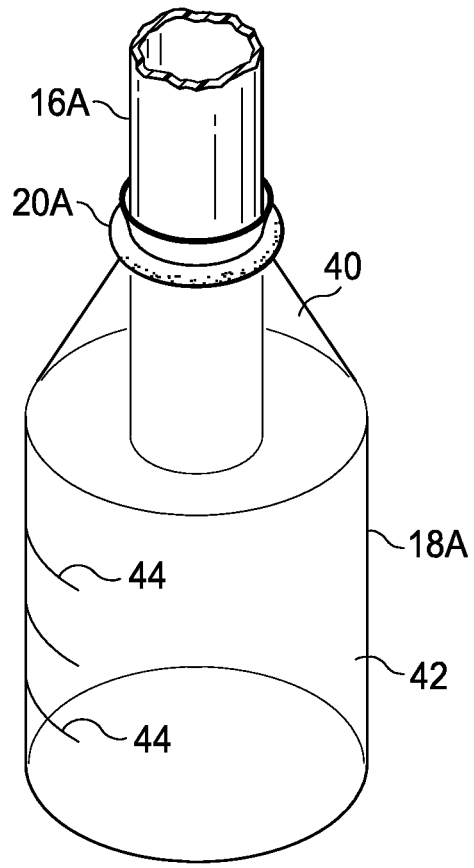
FIG. 7 is a simplified diagram illustrating yet other example details of an embodiment of the system.

Turning to FIG. 7, FIG. 7 is a simplified diagram illustrating example details of an embodiment of system 10. Example container 18A may comprise a flexible portion 40 and an inflexible portion 42. Flexible portion 40 may be clamped on to example tube 16A using example elastic valve 20A. In some embodiments, container 18A may comprise volumetric measurement markings 44. When fluid fills container 18A to a desired volume, for example, as indicated by volumetric measurement marking 44, container 18A may be detached from tube 16A, whereupon elastic valve 20A may close container 18A, sealing the fluid inside.

Figure 8:
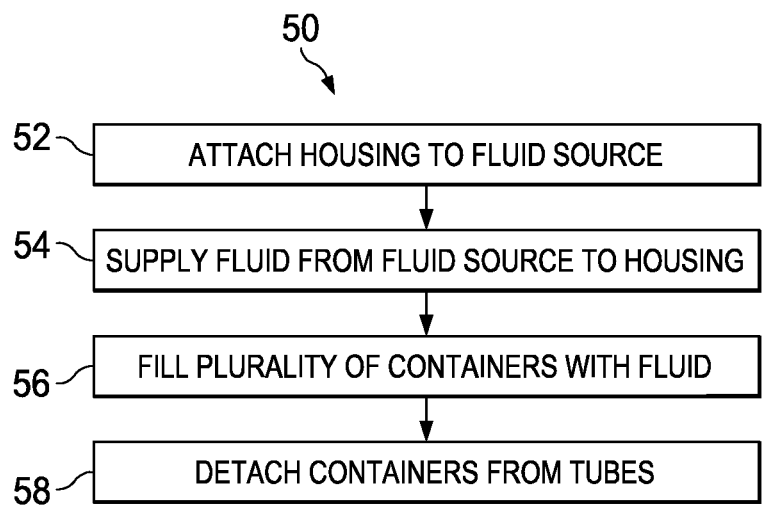
FIG. 8 is a simplified flow diagram illustrating example operations that may be associated with an embodiment of the system.

Turning to FIG. 8, FIG. 8 is a simplified flow diagram 50 illustrating example operations that may be associated with an embodiment of system 10. At 52, housing 12 may be attached to a fluid source (e.g., through hose 14, spigot 33, etc.) At 54, fluid may be supplied from the fluid source to housing 12. At 56, plurality of containers 18 may be filled with the fluid. At 58, containers 18 may be detached from corresponding tubes 16.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

The elements described herein may be made of any suitable materials, including metal (e.g., stainless steel, copper, brass, bronze, aluminum, etc.), plastic, glass, elastomers, or any suitable combination thereof. Each element may also be made of a combination of different materials (e.g., housing and tubes may be made of plastic and containers may be made of elastic rubber; housing and tubes may be made of stainless steel and containers may be made of a combination of glass and flexible plastic; etc.). Any suitable material or combination of materials may be used for the components described herein without departing from the broad scope of the present disclosure.

In addition, the shapes shown and illustrated in the various FIGURES are for example purposes only. Various other shapes may be used herein without changing the scope of the present disclosure. For example, housing 12 may be conical, cylindrical, pyramidal, etc., without departing from the broad scope of the embodiments. Likewise, tubes 16 may be rigid, or flexible 18 without departing from the scope of the broad embodiments.

While the disclosure references several particular embodiments, those skilled in the art will be able to make various modifications to the described embodiments without departing from the true spirit and scope of the disclosure. It is intended that all elements or steps which are insubstantially different from those recited in the claims but perform substantially the same functions, respectively, in substantially the same way to achieve the same result as what is claimed are within the scope of the disclosure.

What is claimed is:

1. An apparatus comprising:
a housing comprising an opening at a first end, and a plurality of holes extending through a common face of the housing at a second end;
a plurality of flexible hollow tubes, each hollow tube attached to the housing at a respective one of the holes at the second end of the housing;
a plurality of containers, each container removably attached to a respective one of the hollow tubes; and
a plurality of elastic fasteners, each elastic fastener clamping a respective one of the plurality of containers to a corresponding hollow tube, and each elastic fastener configured to provide a connecting force that is not less than a weight of one of the containers when substantially filled with water, and to automatically seal its respective one of the plurality of containers upon detaching the container from its corresponding hollow tube, such that shaking the hollow tubes in a state in which the containers are substantially filled with water overcomes the connecting force and causes the containers to detach from the hollow tubes thereby causing the elastic fasteners to automatically seal the containers,
wherein the apparatus is configured to fill the containers substantially simultaneously with a fluid.

2. The apparatus of claim 1, wherein the first end of the housing has an outermost perimeter that is smaller in length than an outermost perimeter of second end.

3. The apparatus of claim 1, wherein the opening at the first end of the housing has a threaded inner surface.

4. The apparatus of claim 1, wherein each container comprises an expandable balloon portion.

5. The apparatus of claim 1, wherein each container comprises a rigid portion and a flexible portion, the flexible portion disposed between the clamp and the respective one of the plurality of tubes.

6. The apparatus of claim 1, wherein each container comprises a volumetric measurement marking providing a visual reference for filling the container to a desired volume.

7. The apparatus of claim 1, wherein the clamp is disposed outwardly from the container and clamps an inner surface of the container against an outer surface of the respective one of the plurality of tubes.

8. The apparatus of claim 1, wherein the fluid comprises one or more of water, air and helium.

9. The apparatus of claim 1, wherein each clamp comprises an O-ring configured to automatically seal the container in response to a force applied to the container in a direction away from the housing.

10. The apparatus of claim 1, wherein the plurality of tubes comprise a first set of tubes each having a first length, and a second set of tubes each having a second length longer than the first length.

11. The apparatus of claim 1, wherein the housing is attached to a valve coupled to a fluid source, wherein the valve is configured to control delivery of the fluid to fill the plurality of containers.

12. The apparatus of claim 11, wherein the valve includes a lever that can be turned to a first position to turn on the valve and allow fluid flow to the housing, wherein the lever can be turned to a second position to turn off the value and stop fluid flow to the housing.

13. The apparatus of claim 11, wherein one end of the valve is connected to a hose attached to a water supply, and the other end is threaded to the housing.

14. The apparatus of claim 1, wherein each hole at the second end of the housing extends through an outer surface of the housing, the outer surface opposing the opening at the first end of the housing.

\* \* \* \* \*

Disclaimer

9,051,066 B1 - Joshua Malone, Plano, TX (US). SYSTEM AND METHOD FOR FILLING CONTAINERS WITH FLUIDS. Patent dated Jun. 9, 2015. Disclaimer filed October 7, 2015, by the assignee, Tinnus Enterprises, LLC.

I hereby disclaim the following complete Claims 7 and 9 of said patent.

*(Official Gazette, February 27, 2024)*